(12) United States Patent
Seely et al.

(10) Patent No.: US 6,667,020 B2
(45) Date of Patent: *Dec. 23, 2003

(54) AMMOXIDATION OF A MIXTURE OF KETONES TO ACETONITRILE AND HCN

(75) Inventors: Michael J. Seely, Twinsburg, OH (US); Sanjay Purushottam Godbole, Solon, OH (US); Dev Dhanaraj Suresh, Hudson, OH (US)

(73) Assignee: The Standard Oil Company, Warrenville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/016,703

(22) Filed: Dec. 10, 2001

(65) Prior Publication Data

US 2003/0198586 A1 Oct. 23, 2003

Related U.S. Application Data

(63) Continuation of application No. 09/320,937, filed on May 27, 1999, now Pat. No. 6,413,485.

(51) Int. Cl.[7] .................................................. C01C 3/02
(52) U.S. Cl. ........................ 423/376; 558/315; 558/319; 558/320; 558/322; 558/323; 558/324; 558/325; 558/326
(58) Field of Search ........................... 423/376; 558/319, 558/320, 315, 322, 323, 324, 325, 326

(56) References Cited

U.S. PATENT DOCUMENTS

| 2,006,981 | A | * | 7/1935 | Andrussow | 423/376 |
| 5,204,079 | A | * | 4/1993 | Suresh et al. | 423/376 |
| 5,973,186 | A | * | 10/1999 | Midorikawa et al. | 558/319 |

* cited by examiner

*Primary Examiner*—Wayne A. Langel
(74) *Attorney, Agent, or Firm*—Thomas E. Nemo

(57) ABSTRACT

A process increasing the yield of both HCN and acetonitrile produced during the manufacture of acrylonitrile comprising introducing a hydrocarbon selected from the group consisting of propylene and propane, a crude ketone and/or a mixture of at least two ketones, ammonia and air, into a reaction zone containing an ammoxidation catalyst, reacting the. hydrocarbon, the ketone, ammonia and oxygen over said catalyst at an elevated temperature to produce acrylonitrile, hydrogen cyanide and acetonitrile, and recovering the acrylonitrile, hydrogen cyanide and acetonitrile from the reactor.

26 Claims, No Drawings

AMMOXIDATION OF A MIXTURE OF KETONES TO ACETONITRILE AND HCN

This application is a continuation of application Ser. No. 09/320,937 filed May 27, 1999, now U.S. Pat. No. 6,413,485.

BACKGROUND OF THE INVENTION

The present invention is directed to a novel process for the ammoxidation of a mixture of ketones to a mixture of nitrites. In particular, the present invention is directed to increasing the yield of co-product hydrogen cyanide and acetonitrile produced during the ammoxidation of propylene to acrylonitrile.

There are patents which address the issue of the injection of acetone into a fluid bed reactor to produce acetonitrile. In addition, these references further disclose that the acetone may be introduced into a fluid bed reactor to increase the co-product acetonitrile while manufacturing acrylonitrile. In particular, Japanese Patent Application 2[1990]-38,333 is directed to improving acetonitrile yields by injecting acetone and/or ethyl alcohol into ammoxidation reactor containing ammoxidation catalyst. The process disclosed in the Japanese Patent Application includes simultaneously injecting the acetone and/or ethyl alcohol into the ammoxidation reactor while manufacturing acrylonitrile.

The present invention is directed to a process which increases the yield of both main co-products (i.e. HCN and acetonitrile) during the manufacture of acrylonitrile while (1) saving on the raw material costs associated with the increase in co-product yields and (2) achieving the same or better conversion and selectivity to the desired co-products.

SUMMARY OF THE INVENTION

It is an object of the present invention to provide a process for the ammoxidation of a mixture of ketones and/or a crude ketone to hydrogen cyanide and acetonitrile.

It is another object of the present invention to provide a process for substantially increasing the yields of co-product hydrogen cyanide and acetonitrile produced during the manufacture of acrylonitrile from propylene.

It is a further object of the present invention to provide a process for the conversion of a mixture of ketones (e.g. acetone and methyl isobutyl ketone (MIBK)) into hydrogen cyanide and acetonitrile during the manufacture of acrylonitrile without substantially affecting the yield of the acrylonitrile.

Additional objects and advantages and novel features of the invention will be set forth in part in the description which follows, and in part will become apparent to those skilled in the art upon examination of the following, or may be learned by the practice of the invention. The objects and advantages of the invention may be realized and attained by means of the instrumentalities and combinations particularly pointed out in the appended claims.

To achieve the foregoing objects in accordance with the purpose of the present invention as broadly described herein, the method of the present invention comprises introducing a hydrocarbon selected from the group consisting of propylene and propane, a mixture of ketones (e.g. acetone and MIBK), ammonia and oxygen-containing gas into reaction zone (e.g fluid bed reactor)to react in the presence of a catalyst (e.g. fluid bed catalyst) to produce a reactor effluent comprising acrylonitrile, hydrogen cyanide and acetonitrile, passing the reactor effluent containing acrylonitrile, hydrogen cyanide and acetonitrile into a quench column to cool the reactor effluent, and recovering the acrylonitrile, acetonitrile and hydrogen cyanide from the quench column.

In another aspect of the present invention, the process comprises introducing a mixture of ketones (e.g. acetone and MIBK) and/or a crude ketone, ammonia and oxygen-containing gas into reaction zone (e.g. fluid bed reactor) to react in the presence of a catalyst (e.g. fluid bed catalyst) to produce a reactor effluent comprising hydrogen cyanide and acetonitrile, passing the reactor effluent containing the hydrogen cyanide and acetonitrile into a quench column to cool the reactor effluent, and recovering the acetonitrile and hydrogen cyanide from the quench column. In the practice of this aspect of the present invention the ammoxidation conditions used in the manufacture of acrylonitrile as disclosed in U.S. Pat. No. 3,911,089 herein incorporated by reference may be utilized.

For purposes of the present invention, the mixture of ketones is intended to include mixtures of commercially available ketones such as acetone, MIBK, methyl ethyl ketone etc. in either their purified, substantially purified, or crude form. In addition, commercially available crude ketones may be used by itself in the practice of the present invention. For purposes of this application the term"crude ketone" shall mean a mixture of at least two ketones and a diluent (e.g. crude acetone shall comprises primarily acetone containing other ketones as impurities and water as a diluent).

In the practice of the present invention, it is envisioned that any ammoxidation catalyst can be utilized to achieve the desired results. Typical ammoxidation catalysts can be generalized by the following two formulae:

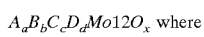

$A_a B_b C_c D_d Mo12O_x$ where

A=Li, Na, K, Cs, T1 and combinations thereof, preferably Cs and K

B=Ni, Co, Mn, Mg, Ca and combinations thereof, preferably Ni, Co and Mg

C=Fe, Cr, Ce, Cu, V, Sb, W, Sn, Ga, Ge, In, P and combinations thereof, preferably Fe, Cr and Ce D=Bi and/or Te, preferably Bi a=0.1–4.0, preferably 0.1 to 0.5, especially preferred being 0.1 to 0.2 b=0.1–10.0, preferably 5 to 9, especially preferred being 6 to 8, and c,d=0.1–10.0, preferably 0.5 to 4, especially preferred being 0.5 to 3; and

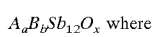

$A_a B_b Sb_{12}O_x$ where

A=Fe, Cr, Ce, V, U, Sn, Ti, Nb and combinations thereof, preferably Fe, V, Sn and Ti B=Mo, W, Co, Cu, Te, Bi, Zn, B, Ni, Ca, Ta and combinations thereof, preferably Mo and Cu a=0.1–16, preferably 2 to 12, especially preferred being 4 to 10 b=0.0–12, preferably 1 to 10, especially preferred being 2 to 6, and the value of x depends on the oxidation state of the elements used.

The catalyst can be used either unsupported, or be supported with silica, alumina, titania, zirconia and the like; however, silica is the preferred support. Typically, catalysts envisioned as suitable in the practice of the present invention are disclosed in U.S. Pat. Nos. 3,642,930; 4,485,079; 3,911, 089, 4,873,215; 5,134,105 and 5,093,299, herein incorporated by reference.

Reference will now be made in detail to the present preferred embodiments of the invention.

DETAILED DESCRIPTION OF THE INVENTION

The present invention is primarily directed to the utilization of a mixture of at least two ketones such as acetone and methyl isobutyl ketone as a source for the production of useful nitrile co-products (hydrogen cyanide and acetonitrile) produced during the manufacture of acrylonitrile. However, the process of the present invention is also applicable to the manufacture of on purpose acetonitrile and hydrogen cyanide by the direct ammoxidation of a mixture of $C_1$ to $C_4$ ketone and/or a crude ketone, ammonia and oxygen in a reaction zone in the presence of an ammoxidation catalyst. In addition, crude ketone (as defined above), by itself, may be utilized in the practice of the present invention thereby further reducing the cost of the raw materials suitable for the production of viable co-products.

The practice of the process of the present invention during the manufacture of acrylonitrile increases the yield of both HCN and acetonitrile during the manufacture of acrylonitrile. The practice of this aspect of the present invention comprises introducing a hydrocarbon selected from the group consisting of propylene and propane, a crude ketone, ammonia and air, into a reaction zone containing an ammoxidation catalyst, reacting the hydrocarbon, ketone, ammonia and oxygen over said catalyst at an elevated temperature to produce acrylonitrile, hydrogen cyanide and acetonitrile, and recovering the acrylonitrile, hydrogen cyanide and acetonitrile from the reactor.

In another embodiment of this aspect of the present invention, the process comprises introducing a hydrocarbon selected from the group consisting of propylene and propane, a mixture of at least two $C_1$ to $C_4$ ketones, ammonia and air, into a reaction zone containing an ammoxidation catalyst, reacting the hydrocarbon, ketones, ammonia and oxygen over said catalyst at an elevated temperature to produce acrylonitrile, hydrogen cyanide and acetonitrile, and recovering the acrylonitrile, hydrogen cyanide and acetonitrile from the reactor.

In the preferred embodiment of this aspect of the present invention, it is necessary that the reactor conditions be adjusted to obtain the increased yield in acetonitrile and hydrogen cyanide obtained by utilizing the mixture of ketones and/or crude ketone. In the practice of the present invention, the ammoxidation reaction conditions should be within the following parameters: Crude ketone is between 1 and 50% of propylene or propane rate on a total carbon basis. The temperature of the reaction is between 410° to 460° C., preferably 405° to 440° C. Typically, the pressure is maintained at between 1 to 5 atmospheres with 1 to 3 atmospheres being preferred.

In a further preferred embodiment of this aspect of the present invention the crude ketone mixture comprises a mixture containing acetone, MIBK and water.

In a still further preferred embodiment of this aspect of the present invention the process is performed in a fluid bed reactor.

In another preferred embodiment of this aspect of the present invention the mixture of ketones comprises crude ketone in combination with at least one substantially pure $C_1$ to $C_4$ ketone.

In still another preferred embodiment of this aspect of the present invention, the ketone is separately introduced into the reactor zone.

In a still further preferred embodiment of this aspect of the present invention, the mixture of ketones and/or crude ketone is separately introduced into the fluid bed reactor, preferably at a location above the point where the hydrocarbon is fed into the reactor, especially preferred being a location in the upper portion of the reactor.

The following examples are set forth below for illustrative purposes and are not considered as limiting to the practice of the present invention. The catalyst utilized in all of the examples was a promoted $BiFeMoO_x$ known for its suitability in the ammoxidation of propylene to acrylonitrile. Five, 10 and 15% of the propylene feed (in terms of total carbon) was replaced with a ketone to give the results set forth below in Table I. In each of the following examples the reactor temperature was 430° C., the pressure was 9.5 psig and the feed ratio of propylene+alcohol/ammonia/air was 1/1.2/9.3. The wwh was 0.06 (grams of hydrocarbon/grams of catalyst-hour)

TABLE I

| Example No. | % Acetone as C Fed | % AN Yield | % Aceto Yield | % HCN Yield |
|---|---|---|---|---|
| 1 (comp.) | 0 | 78.6 | 2.0 | 6.7 |
| 2 | 5 | 75.5 | 3.1 | 7.5 |
| 3 | 10 | 72.3 | 4.1 | 8.4 |
| 4 | 15 | 68.3 | 5.2 | 9.6 |

As a further example of the value of using crude ketones, 10% by weight water was blended with the acetone above and this was co-fed to the same propylene ammoxidation reactor. The results are shown below in Table II and indicate that water dilution has no deleterious effect on performance.

TABLE II

| Example No. | % Blend as C Fed | % AN Yield | % Aceto Yield | % HCN Yield |
|---|---|---|---|---|
| 5 (comp.) | 0 | 78.9 | 2.0 | 6.6 |
| 6 | 5 | 75.3 | 3.2 | 7.8 |
| 7 | 10 | 71.7 | 4.2 | 8.7 |
| 8 | 15 | 67.5 | 5.3 | 9.6 |

In general, all ketones can be ammoxidized to a mixture of nitrites. The preferred ketones include $C_1$ to $C_4$ ketones. The following example illustrates the use of a C4 ketone in the form of methyl ethyl ketone (MEK).

TABLE III

| Example No. | % MEK as C Fed | % AN Yield | % Aceto Yield | % HCN Yield |
|---|---|---|---|---|
| 9 (comp.) | 0 | 79.2 | 2.1 | 6.9 |
| 10 | 2.5 | 77.6 | 3.2 | 7.0 |
| 11 | 5 | 75.5 | 4.2 | 7.4 |

The following examples are illustrative of the practice of the present invention for direct ammoxidation of ketones to acetonitrile and HCN. The feed ratio for the ketone/ammonia/air used in Example 12 and 13 were 1/1.7/13.1 and 1/2/15.1 respectively. The temperature of the reaction was 413° C. for Example 12 and 411° C. for Example 13. The reactor pressure was 10 psig for both examples and the wwh was 0.133 and 0.149 for Examples 12 and 13, respectively. Table IV below sets forth the results for Examples 12 and 13.

TABLE IV

| Example No. | ketone | % Conversion | % Aceto Yield | % HCN Yield |
|---|---|---|---|---|
| 12 | acetone | 98.9 | 28.0 | 27.8 |
| 13 | methyl ethyl ketone | 99.9 | 46.0 | 16.5 |

While the examples are illustrative of the practice of the present invention, they are not intended to limit applicants' invention to that illustrated and obviously many modifications and variations may be utilized in light of the above teaching. It is intended that the scope of applicants' invention be defined by the claims appended hereto.

What we claim as our invention is:

1. A process for increasing the yield of co-product HCN and acetonitrile produced during the manufacture of acrylonitrile comprising introducing a hydrocarbon selected from the group consisting of propylene and propane, a crude ketone, ammonia and an oxygen-containing gas into a reaction zone containing an ammoxidation catalyst, reacting the hydrocarbon, crude ketone, ammonia and oxygen over said catalyst at an elevated temperature to produce acrylonitrile, hydrogen cyanide and acetonitrile, and recovering the acrylonitrile, hydrogen cyanide and acetonitrile from the reaction zone.

2. The process of claim 1 wherein the feed ratio of hydrocarbon: ketone ranges from 1:0.01 to 1:0.5, on a total carbon basis.

3. The process of claim 2 wherein the temperature ranges from 410° C. to 460° C. and the hydrocarbon is propane.

4. The process of claim 3 wherein the temperature ranges from 430° to 450° C.

5. The process of claim 4 wherein the pressure ranges from 1 to 5 atmospheres.

6. The process of claim 3 wherein the pressure ranges from 1 to 5 atmospheres.

7. The process of claim 1 wherein the crude ketone comprises crude acetone.

8. The process of claim 7 wherein the hydrocarbon comprises propane.

9. The process of claim 1 wherein the crude ketone comprises a mixture of at least two $C_1$ to $C_4$ ketones and water.

10. The process of claim 1 wherein the ammoxidation catalyst is characterized by the following formula:

$$A_aB_bC_cD_dMo_{12}O_x \text{ where}$$

A=Li, Na, K, Cs, Tl and combinations thereof
B=Ni, Co, Mn, Mg, Ca and combinations thereof
C=Fe, Cr, Ce, Cu, V, Sb, W, Sn, Ga, Ge, In, P and combinations thereof
D=Bi and/or Te,
a=0.1–4.0,
b=0.1–10.0, and
c,d=0.1–10.0.

11. The process of claim 1 wherein the ammoxidation catalyst is characterized by the following formula:

$$A_aB_bSb_{12}O_x \text{ where}$$

A=Fe, Cr, Ce, V, U, Sn, Ti, Nb and combinations thereof
B=Mo, W, Co, Cu, Te, Bi, Zn, B, Ni, Ca, Ta and combinations thereof
a=0.1–16,
b=0.0–12, and the value of x depends on the oxidation state of the elements used.

12. The process of claim 1 wherein the hydrocarbon comprises propane.

13. The process of claim 2 wherein the hydrocarbon comprises propane.

14. A process for increasing the yield of co-product HCN and acetonitrile produced during the manufacture of acrylonitrile comprising introducing a hydrocarbon selected from the group consisting of propylene and propane, a mixture of at least two ketones, ammonia and an oxygen-containing gas into a reaction zone containing an ammoxidation catalyst, reacting the hydrocarbon, ketones, ammonia and oxygen over said catalyst at an elevated temperature to produce acrylonitrile, hydrogen cyanide and acetonitrile, and recovering the acrylonitrile, hydrogen cyanide and acetonitrile from the reaction zone.

15. The process of claim 14 wherein the mixture of ketones comprises a crude ketone and at least one substantially pure $C_1$ to $C_4$ ketone.

16. The process of claim 15 wherein the temperature ranges from 410° C. to 460° C. and the hydrocarbon is propane.

17. The process of claim 16 wherein the temperature ranges from 430° to 450° C.

18. The process of claim 17 wherein the pressure ranges from 1 to 5 atmospheres.

19. The process of claim 16 wherein the pressure ranges from 1 to 5 atmospheres.

20. The process of claim 14 wherein the mixture of ketones comprises at least two $C_1$ to $C_4$ ketones.

21. The process of claim 20 wherein the mixture of ketones comprises acetone and methyl isobutyl ketone.

22. The process of claim 14 wherein the ammoxidation catalyst is characterized by the following formula:

$$A_aB_bC_cD_dMo_{12}O_x \text{ where}$$

A=Li, Na, K, Cs, Tl and combinations thereof
B=Ni, Co, Mn, Mg, Ca and combinations thereof
C=Fe, Cr, Ce, Cu, V, Sb, W, Sn, Ga, Ge, In, P and combinations thereof
D=Bi and/or Te,
a=0.1–4.0,
b=0.1–10.0, and
c,d=0.1–10.0.

23. The process of claim 14 wherein the ammoxidation catalyst is characterized by the following formula:

$$A_aB_bSb_{12}O_x \text{ where}$$

A=Fe, Cr, Ce, V, U, Sn, Ti, Nb and combinations thereof
B=Mo, W, Co, Cu, Te, Bi, Zn, B, Ni, Ca, Ta and combinations thereof
a=0.1–16,
b=0.0–12, and
the value of x depends on the oxidation state of the elements used.

24. The process of claim 14 wherein the hydrocarbon comprises propane.

25. A process for the ammoxidation of a mixture of $C_1$ to $C_4$ ketones to produce HCN and acetonitrile comprising introducing the mixture of ketones, ammonia and an oxygen-containing gas into a reaction zone containing an ammoxidation catalyst, reacting the ketones, ammonia and oxygen over said catalyst at an elevated temperature to produce hydrogen cyanide and acetonitrile, and recovering the hydrogen cyanide and acetonitrile from the reaction zone.

26. A process for the ammoxidation of a crude ketone to produce HCN and acetonitrile comprising introducing the crude ketone, ammonia and an oxygen-containing gas into a reaction zone containing an ammoxidation catalyst, reacting the ketone, ammonia and oxygen over said catalyst at an elevated temperature to produce hydrogen cyanide and acetonitrile, and recovering the hydrogen cyanide and acetonitrile from the reaction zone.

* * * * *